United States Patent
Yano et al.

(10) Patent No.: US 7,157,432 B2
(45) Date of Patent: *Jan. 2, 2007

(54) TETRAPHENYLBACTERIOCHLORIN DERIVATIVES AND COMPOSITIONS CONTAINING THE SAME

(75) Inventors: Shigenobu Yano, 5-730-514, Gakuenyamatocho, Nara-shi, Nara 631-0041 (JP); Toyoji Kakuchi, Sapporo (JP); Yuji Mikata, Nara (JP)

(73) Assignees: San-Ei Gen F.F.I., Inc., Osaka (JP); Shigenobu Yano, Nara (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/219,853

(22) Filed: Sep. 7, 2005

(65) Prior Publication Data

US 2006/0003946 A1 Jan. 5, 2006

Related U.S. Application Data

(62) Division of application No. 10/363,824, filed on Mar. 7, 2003, now Pat. No. 6,958,389.

(60) Provisional application No. PCT/JP01/07758, filed on Sep. 6, 2001.

(30) Foreign Application Priority Data

Sep. 8, 2000 (JP) ............................. 2000-273649

(51) Int. Cl.
*A61K 31/70* (2006.01)
*C07H 1/00* (2006.01)
*C07H 17/00* (2006.01)

(52) U.S. Cl. ..................... 514/25; 536/17.1; 536/17.4; 536/18.5

(58) Field of Classification Search ............... 536/17.1, 536/17.4, 18.5; 514/25
See application file for complete search history.

(56) References Cited

FOREIGN PATENT DOCUMENTS

JP 2000-007693 A 1/2000
WO WO-96/13504 A1 5/1996

OTHER PUBLICATIONS

R.P. Bonar-Law et al., J. Chem. Soc., Chem. Commun., pp. 456-458 (1993).
N. Datta-Gupta et al., J. Org. Chem., vol. 36, No. 14, pp. 2019-2021 (1971).
L. Gong et al., Can. J. Chem., vol. 63, pp. 401-405 (1985).
X. Zhang et al., Journal of Molecular Catalysis A: Chemical, vol. 154, pp. 31-38 (1999).
Y. Mitaka et al., Tetrahedron Letters, vol. 39, pp. 4505-4508 (1998).
H.W. Whitlock et al., Journal of the American Chemical Society, vol. 91, No. 26, Dec. 17, 1969, pp. 7485-7489.

*Primary Examiner*—Elli Peselev
(74) *Attorney, Agent, or Firm*—Birch, Stewart, Kolasch, and Birch, LLP

(57) ABSTRACT

Provided is a tetraphenylbacteriochlorin derivative represented by the formula (I):

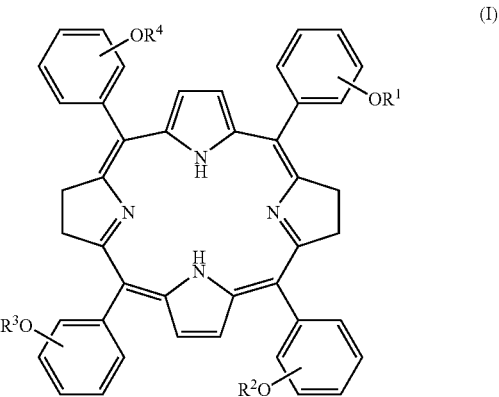

[wherein $R^1$, $R^2$, $R^3$ and $R^4$, independently from each other, are a residue of a monosaccharide represented by the formulae:

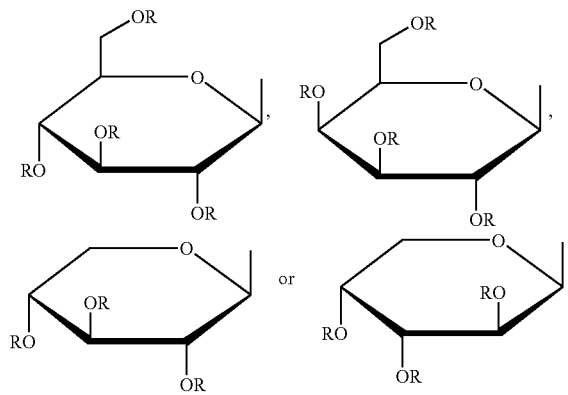

(wherein, R is a hydrogen or a protecting group)], or its salt. The tetraphenylbacteriochlorin derivative or its salt has a large molar extinction coefficient at long wavelengths which are expected to have a high tissue-penetrating property, and exhibits high selectivity to tumor cells and hydrophilicity.

5 Claims, 2 Drawing Sheets

TETRAPHENYLBACTERIOCHLORIN DERIVATIVES AND COMPOSITIONS CONTAINING THE SAME

This application is a Divisional of application Ser. No. 10/363,824 filed on Mar. 7, 2003, now U.S. Pat. No. 6,958,389 issued Oct. 25, 2005 and for which priority is claimed under 35 U.S.C. § 120. Application Ser. No. 10/363,824 is the national phase of PCT International Application No. PCT/JP01/07758 filed on Sep. 6, 2001 under 35 U.S.C. § 371. The entire contents of each of the above-identified applications are hereby incorporated by reference.

TECHNICAL FIELD

The present invention relates to tetraphenylbacteriochlorin derivatives, particularly, tetraphenylbacteriochlorin derivatives substituted by monosaccharide residues and their salts, a method of producing the same and compositions as photosensitizers containing the same, especially compositions usable for photodynamic therapy (PDT).

BACKGROUND ART

The photodynamic therapy (PDT), according to which photosensitizers having a specific affinity for tumor cells are administered to patients before irradiation by laser beams of various wavelengths for treatment of cancers, is now attracting attention as a non-invasive therapy for cancers. Known photosensitizers usable for the PDT include various derivative compounds having a porphyrin skeleton, some of which are used clinically.

Desirable photosensitizers usable for PDT are required to be hydrophilic and highly selective to tumor cells and to have a large molar extinction coefficient at a long-wavelength range. Long wavelength light shows a good penetrating property to tissues and allows the use of an inexpensive laser irradiator. However, the porphyrin derivatives proposed so far have problems such as their hydrophobicity that causes side effects and their small molar extinction coefficient for long-wavelength light range. Therefore, the development of superior photosensitizers is desired.

For the purpose of solving these problems, Japanese Unexamined Patent Publication No. 2000-7693 generally discloses hydrophilic tetraphenylchlorin derivatives and bacteriochlorin derivatives with saccharide residues on phenyl groups which have a larger molar extinction coefficient to the long-wavelength light compared to the porphyrin derivatives. However, the publication does not actually disclose the synthesis of the bacteriochlorin derivatives and their effects as photosensitizers.

DISCLOSURE OF INVENTION

As a result of extensive study for development of better photosensitizer, an object of the present invention is to provide a novel derivative having tetraphenylbacteriochlorin as a core structure, which has a large molar extinction coefficient at the long-wavelength region and is expected to exhibit a high tissue penetrating property, and having a monosaccharide residue as a substituent, for providing hydrophilicity and high selectivity for tumor cells.

BEST MODE FOR CARRYING OUT THE INVENTION

Figure 1:
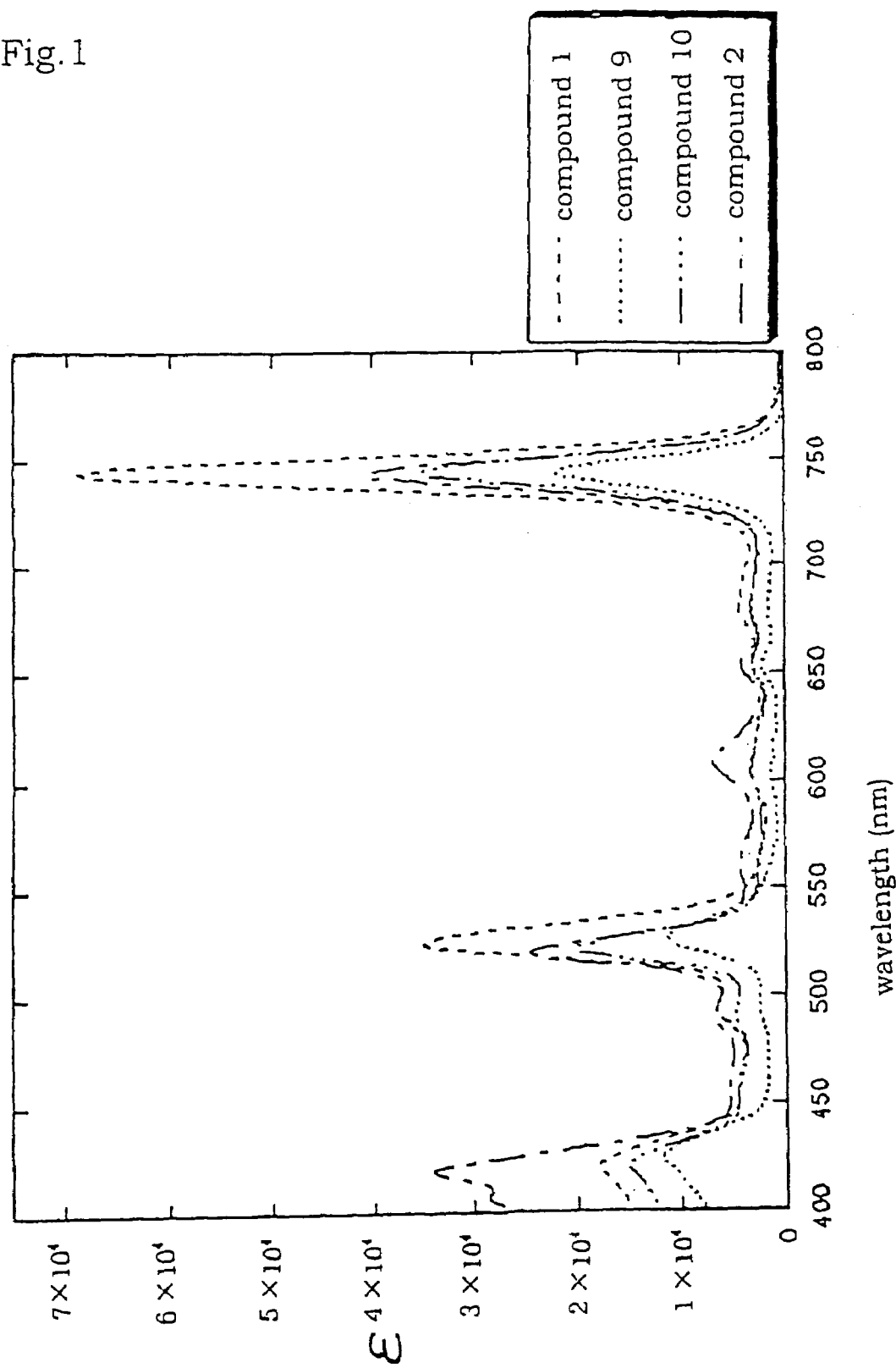
FIG. 1 is a chart showing UV absorption of Compounds 1, 2, 9 and 10 of the present invention.

According to the present invention, provided is a tetraphenylbacteriochlorin derivative represented by the formula (I):

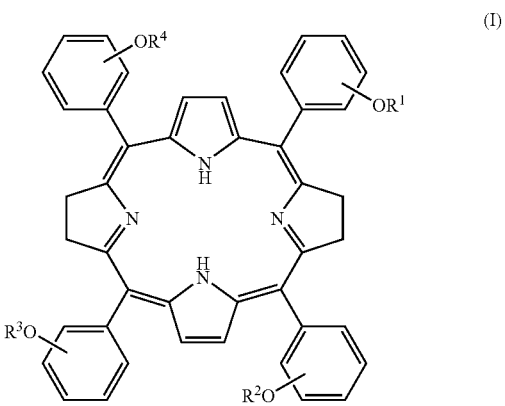

(I)

[wherein, $R^1$, $R^2$, $R^3$ and $R^4$, independently from each other, are residues of monosaccharides represented by the formulae:

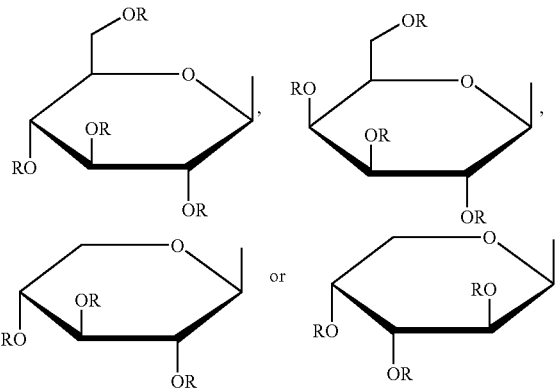

(wherein R is a hydrogen atom or a protecting group)], or their salts.

In the bacteriochlorin derivatives provided by the present invention, all or some of the hydroxyl groups of the monosaccharide residues may be protected by suitable protecting groups for exhibiting a specific cell affinity. As such protecting groups, may be mentioned aliphatic acyl groups having a carbon number of 1 to 10 (for example, formyl, acetyl, propionyl, butyryl, isobutyryl, valeryl, isovaleryl, oxalyl, succinyl, pivaloyl, etc.), aromatic acyl groups (for example, benzoyl, toluoyl, xyloyl, naphthoyl, etc.) and aralkyl groups (for example, benzyl, etc.). Among these protecting groups, the acyl groups are preferable, acyl groups having a carbon number of 2 to 5 are more preferable, and the acetyl group is the most preferable. All or some of these protecting groups may be left without deprotection in consideration of balance of lipophilicity of the whole molecule. In this connection, tetraphenylbacteriochlorin derivatives (I) with some or all the protecting groups remaining are also included in the scope of the present invention.

Preferable examples of monosaccharide residues include:
2,3,4,6-tetra-O-acetyl-α-D-glucopyranosyl,
2,3,4,6-tetra-O-acetyl-β-D-glucopyranosyl,
2,3,4,6-tetra-O-propionyl-α-D-glucopyranosyl,
2,3,4,6-tetra-O-propionyl-β-D-glucopyranosyl,
2,3,4,6-tetra-O-butyryl-α-D-glucopyranosyl,
2,3,4,6-tetra-O-butyryl-β-D-glucopyranosyl,
2,3,4,6-tetra-O-isobutyryl-α-D-glucopyranosyl,
2,3,4,6-tetra-O-isobutyryl-β-D-glucopyranosyl,
2,3,4,6-tetra-O-acetyl-α-D-galactopyranosyl,
2,3,4,6-tetra-O-acetyl-β-D-galactopyranosyl,
2,3,4,6-tetra-O-propionyl-α-D-galactopyranosyl,
2,3,4,6-tetra-O-propionyl-β-D-galactopyranosyl,
2,3,4,6-tetra-O-butyryl-α-D-galactopyranosyl,
2,3,4,6-tetra-O-butyryl-β-D-galactopyranosyl,
2,3,4,6-tetra-O-isobutyryl-α-D-galactopyranosyl,
2,3,4,6-tetra-O-isobutyryl-β-D-galactopyranosyl,
2,3,4-tri-O-acetyl-α-D-arabinopyranosyl,
2,3,4-tri-O-acetyl-β-D-arabinopyranosyl,
2,3,4-tri-O-propionyl-α-D-arabinopyranosyl,
2,3,4-tri-O-propionyl-β-D-arabinopyranosyl,
2,3,4-tri-O-butyryl-α-D-arabinopyranosyl,
2,3,4-tri-O-butyryl-β-D-arabinopyranosyl,
2,3,4-tri-O-isobutyryl-α-D-arabinopyranosyl,
2,3,4-tri-O-isobutyryl-β-D-arabinopyranosyl,
2,3,4-tri-O-acetyl-α-D-xylopyranosyl,
2,3,4-tri-O-acetyl-β-D-xylopyranosyl,
2,3,4-tri-O-propionyl-α-D-xylopyranosyl,
2,3,4-tri-O-propionyl-β-D-xylopyranosyl,
2,3,4-tri-O-butyryl-α-D-xylopyranosyl,
2,3,4-tri-O-butyryl-β-D-xylopyranosyl,
2,3,4-tri-O-isobutyryl-α-D-xylopyranosyl and
2,3,4-tri-O-isobutyryl-β-D-xylopyranosyl.

These residues of monosaccharides are for providing a desired cell affinity to the tetraphenylbacteriochlorin derivative and are introduced as substituents on phenyl groups via ether linkage. The position of substitution is the o-, m- or p-position of the phenyl groups. The position of substitution is not particularly limited, but the m- and p-positions are preferable.

Preferable examples of tetraphenylbacteriochlorin derivatives (I) according to the present invention are as follows:
5,10,15,20-tetrakis[4-(2',3',4',6'-tetra-O-acetyl-β-D-glucopyranosyl-oxy)phenyl]bacteriochlorin (Compound 1),
5,10,15,20-tetrakis[3-(2',3',4',6'-tetra-O-acetyl-β-D-glucopyranosyl-oxy)phenyl]bacteriochlorin (Compound 2),
5,10,15,20-tetrakis[4-(2',3',4',6'-tetra-O-acetyl-β-D-galactopyranosyloxy)phenyl]bacteriochlorin (Compound 3),
5,10,15,20-tetrakis[3-(2',3',4',6'-tetra-O-acetyl-β-D-galactopyranosyloxy)phenyl]bacteriochlorin (Compound 4),
5,10,15,20-tetrakis[4-(2',3',4'-tri-O-acetyl-β-D-arabinopyranosyloxy)phenyl]bacteriochlorin (Compound 5),
5,10,15,20-tetrakis[3-(2',3',4'-tri-O-acetyl-β-D-arabinopyranosyloxy)phenyl]bacteriochlorin (Compound 6),
5,10,15,20-tetrakis[4-(2',3',4'-tri-O-acetyl-β-D-xylopyranosyloxy)-phenyl]bacteriochlorin (Compound 7)
5,10,15,20-tetrakis[3-(2',3',4'-tri-O-acetyl-β-D-xylopyranosyloxy)-phenyl]bacteriochlorin (Compound 8),
5,10,15,20-tetrakis[4-(β-D-glucopyranosyloxy)phenyl]bacteriochlorin (Compound 9),
5,10,15,20-tetrakis[3-(β-D-glucopyranosyloxy)phenyl]bacteriochlorin (Compound 10),
5,10,15,20-tetrakis[4-(β-D-galactopyranosyloxy)phenyl]bacteriochlorin (Compound 11),
5,10,15,20-tetrakis[3-(β-D-galactopyranosyloxy)phenyl]bacteriochlorin (Compound 12),
5,10,15,20-tetrakis[4-(β-D-arabinopyranosyloxy)phenyl]bacteriochlorin (Compound 13),
5,10,15,20-tetrakis[3-(β-D-arabinopyranosyloxy)phenyl]bacteriochlorin (Compound 14),
5,10,15,20-tetrakis[4-(β-D-xylopyranosyloxy)phenyl]bacteriochlorin (Compound 15) and
5,10,15,20-tetrakis[3-(β-D-xylopyranosyloxy)phenyl]bacteriochlorin (Compound 16).

The tetraphenylbacteriochlorin derivatives (I) of the present invention can be prepared according to the processes described by Bonnett (R. Bonnett, *Chem. Soc. Rev.*, 1995, 24, 19), Whitlock et al (Whitlock, H. W., Hanauser, R., Oester, M. Y. & Bower, B. K., *J. Am. Chem. Soc.*, 1969, 91, 7485), for example, by the process described below. Tetraphenylporphyrin derivatives (II) or their salts as starting materials can be prepared according to the process described by Japanese Unexamined Patent Publication No. 2000-7693:

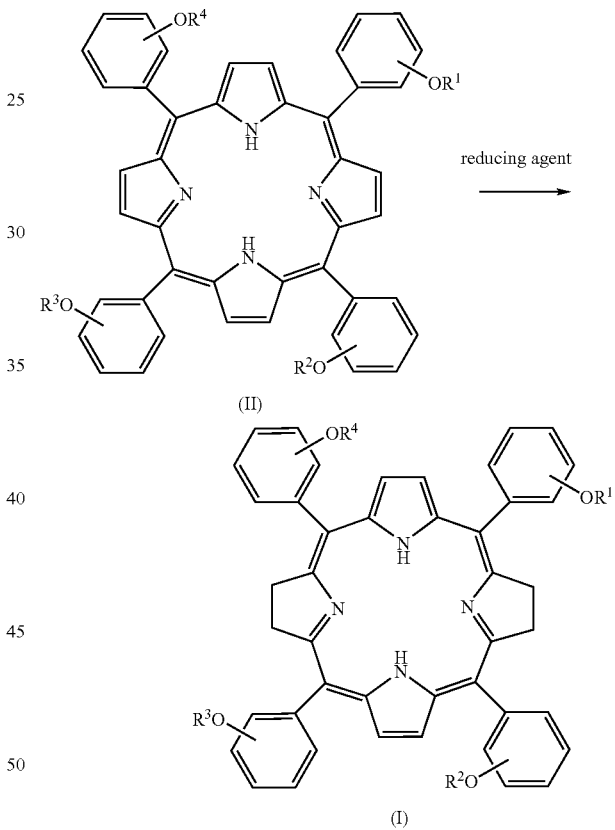

(wherein, $R^1$, $R^2$, $R^3$ and $R^4$ are as define above).

The tetraphenylbacteriochlorin derivatives represented by the formula (I) and their salts can be obtained by reducing tetraphenylporphyrin derivatives represented by the formula (II) or their salts in the presence of one to three equivalents, preferably about three equivalents, of an alkali metal carbonate using a most suitable amount of a reducing agent. The compounds of the present invention can be obtained by reduction using about 40 equivalents of the reducing agent.

As the reducing agent, hydrazone, semicarbane and p-toluenesulfonylhydrazide may be used, among which p-toluenesulfonylhydrazide is preferable. As the alkali metal carbonate, sodium carbonate, potassium carbonate, cesium carbonate and the like may be mentioned, among which potassium carbonate is preferable.

This reaction is preferably carried out in a solvent in an atmosphere of an inert gas such as nitrogen with protection from light. As the reaction solvent, toluene, 1-butanol, diethylene glycol, triethylene glycol, dimethylsulfoxide (stirred at room temperature), pyridine etc may be used. Among these, pyridine is preferable. The reaction temperature is not particularly limited, but may be preferably such that the reaction solvent is heated under reflux.

The reducing agent may be added to a reaction mixture in two or more aliquots. At this time, the reducing agent is preferably added as a solution in the same solvent as the reaction solvent.

The end point of the reaction is usually determined by collecting a small amount of the reaction mixture and judging from the UV spectrum of a diluted aliquot. The judgment of the end point is based on disappearance of absorption specific to the porphyrin skeleton around 650 nm from the UV spectrum of the dilution. At this time, absorption specific to the bacteriochlorin skeleton around 740 nm is usually observed.

Subsequently, if desired, the reaction product is subjected to a deprotection reaction such as alkali treatment depending upon protecting groups of the reaction product in a suitable organic solvent in order to release the protecting groups in the monosaccharide residues of the tetraphenylbacteriochlorin derivatives (I), thereby obtaining the tetraphenylbacteriochlorin derivatives (I) of the present invention in which all or part of the hydroxyl groups are in a free state.

In the case where the protecting groups are acyl groups, the deprotection reaction is performed by a hydrolytic reaction. More particularly, the hydrolytic reaction is performed by treating a protected compound with an alikali such as an alkali metal alkoxide, for example, sodium methoxide, sodium ethoxide, sodium t-butoxide, potassium methoxide, potassium ethoxide, potassium t-butoxide, etc. in chloroform, dichloromethane, methanol, ethanol or a mixed solvent. It is possible to hydrolyze only some of the acyl groups in the monosaccharide residues and leave the other acyl groups remaining by selecting appropriate conditions for the hydrolytic reaction.

Of the starting tetraphenylporphyrin derivatives (II), those in which $R^1$, $R^2$, $R^3$ and $R^4$ are the same and $OR^1$, $OR^2$, $OR^3$ and $OR^4$ are substituted at m-position (i.e., tetraphenylporphyrin derivatives (V) described later) can be prepared according to Adler method of heating under reflux benzaldehyde derivatives (III) described later with and pyrrole in the presence of propionic acid (D. A. James, D. P. Arnold, P. G. Parsons, *Photochem. Photbiol.*, 1994, 59, 441) or according to Lindsey method of moderately reacting benzaldehyde derivatives (III) with pyrrole in the presence of $BF_3.Et_2O$ in a highly diluted solvent (J. Org. Chem., 64, 1391(1999) and 64, 2864 (1999)).

Preferably, according to the present invention, a starting material tetraphenylporphyrin derivative (V) as mentioned above can be prepared in high yield according to the following process:

First, a benzaldehyde derivative (III) is reacted with pyrrole in the presence of a metal compound containing a metal selected from the group I transition metals of the periodic table of elements to produce a tetraphenylporphyrin derivative (IV):

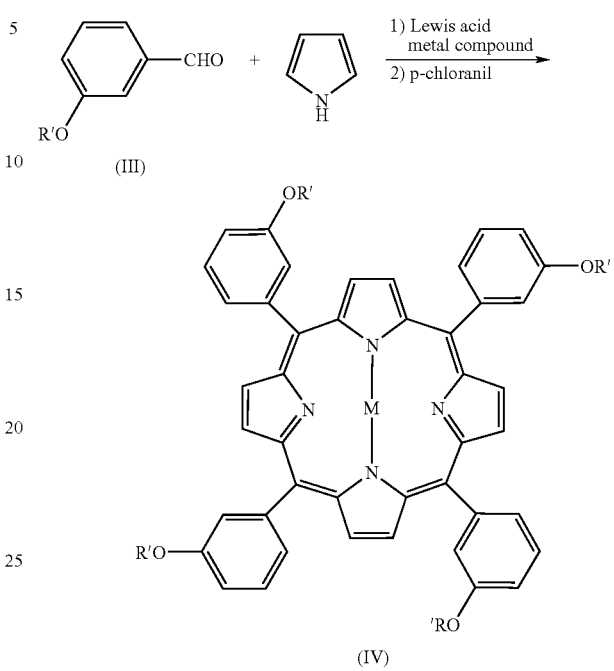

wherein R' is a hydrogen atom, an alkyl group or a monosaccharide residue represented by the formulae:

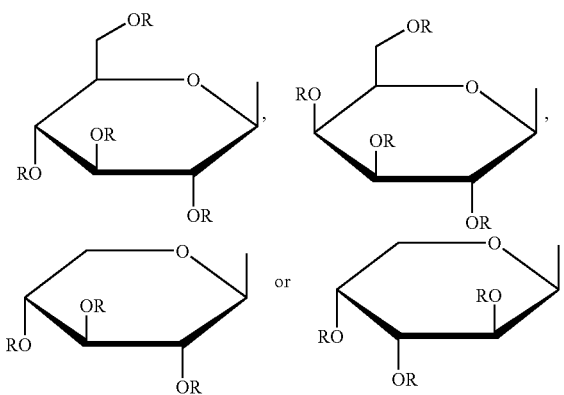

(wherein R is hydrogen or a protecting group), and M is a metal selected from the group I transition metals of the periodic table of elements.

The metal compound is a compound containing a metal selected from the group I transition metals of the periodic table of elements. Particularly, the metal is selected from Sc, Ti, V, Cr, Mn, Fe, Co, Ni, Cu and Zn, among which Zn is preferred. The metal compound may be in the form of an acetate or a halide such as chloride, a bromide or an iodide. More particularly zinc acetate is preferred. The metal compound may be a hydrate or may be solvated with solvents such as ethanol.

The tetraphenylporphyrin derivative (IV) is prepared by stirring about 1 equivalent of the benzaldehyde derivative (III), about 1 equivalent of pyrrole, about two to five equivalents of the metal compound, about 0.1 to 1 equivalents of $BF_3 \cdot Et_2O$ and a Lewis acid such as aluminum chloride with protection from light in an atmosphere of an inert gas such as argon, nitrogen or the like at room temperature for about 1 to 24 hours. As a reaction solvent, a nonpolar organic solvent such as chloroform, methylene chloride or toluene may be used. Subsequently, about 0.1 to 1 equivalents of p-chloranil are added with respect to about 1 equivalent of the benzaldehyde derivative (III) and pyrrole, and the resulting mixture is heated at the reflux temperature of the solvent for about 1 to 5 hours to give the tetraphenylporphyrin derivative (IV).

According to the present invention, the obtained tetraphenylporphyrin derivative (IV) is treated with an acid such as hydrochloric acid at room temperature to 100° C. to demetalize, i.e., to remove metal M to give a tetraphenylporphyrin derivative (V):

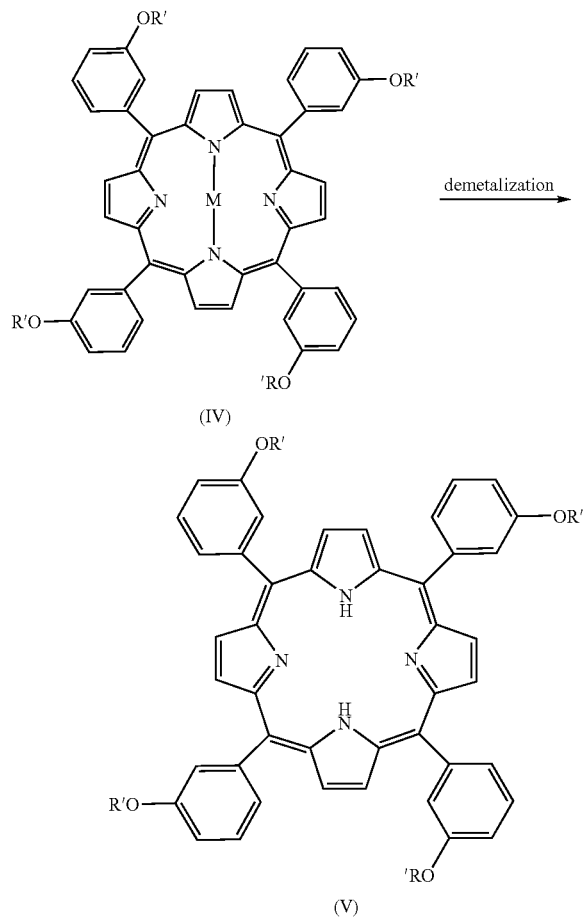

According to the present invention, the tetraphenylporphyrin derivative (V) can be prepared by a continuous process starting with the benzaldehyde derivative (III) and pyrrole without isolating the tetraphenylporphyrin derivative (IV).

By use of the process of the present invention, a tetraphenylporphyrin derivative (V) wherein R' is a hydrogen atom which is a compound known to be able to be used as foscan for PDT (Japanese Patent Publication No. HEI 6(1994)-53665) can be obtained by dealkylation of a tetraphenylporphyrin derivative (V) wherein R' is an alkyl group such as methyl.

As salts of the tetraphenylbacteriochlorin derivatives (I) of the present invention, salts formed with acids or bases and inner complex salts with metals may be mentioned.

The salts formed with acids or bases can be formed by treating the tetraphenylbacteriochlorin derivatives (I) obtained above with appropriate acids or bases. As acids or bases usable for forming the salts, may be mentioned, for example, mineral acids such as hydrochloric acid, hydrobromic acid, nitric acid, sulfuric acid and the like, organic acids such as toluenesulfonic acid, benzenesulfornic acid, hydroxides, carbonates and hydrogencarbonates of alkali metals and alkali-earth metals (e.g., sodium, potassium, calcium and magnesium) and organic bases such as ammonium, trimethylamine, triethylamine may be mentioned.

As metals usable for forming the inner complex salts, alkali metal (e.g., lithium, sodium, potassium, rubidium, cesium), alkali-earth metals (e.g., magnesium, calcium, barium, strontium), the group 3 metals of the periodic table (e.g., scandium, lanthanum, yttrium), lanthanoids (e.g., europium, praseodymium, ytterbium), the group 4 metals (e.g., titanium), the group 5 metals (e.g., vanadium), the group 6 metals (e.g., chromium, molybdenum, tungsten), the group 7 metals (e.g., manganese, rhenium), the group 8 metals (e.g., iron, ruthenium, osmium), the group 9 metals (e.g., cobalt, rhodium, iridium), the group 10 metals (e.g., nickel, palladium, platinum), the group 11 metals (e.g., copper, silver, gold), the group 12 metals (e.g., zinc, cadmium, mercury), the group 13 metals (e.g., aluminum, gallium, indium), the group 14 metals (e.g., silicon, germanium, tin, lead) and the group 15 metals (arsenic, antimony, bismuth), among which the group 10 and 12 metals are preferable, and zinc and platinum are the most preferable. The inner complex salts with metals can be formed by reaction of the tetraphenylbacteriochlorin derivatives (I) with halides, acetates, hydroxides or perchlorates of the metals.

The tetraphenylbacteriochlorin derivatives (I) and their salts are more hydrophilic due to the introduction of the monosaccharide residues and are expected to have selectivity to tumor cells by cell recognition. Furthermore, because the bacteriochlorin skeleton as the core structure of the tetraphenylbacteriochlorin derivative (I) and their salts has an absorption feature near 740 nm which is in the long-wavelength range, compositions containing the tetraphenylbacteriochlorin derivatives (I) and their salts allow affected sites to be irradiated with long-wavelength light. Upon irradiation with long-wavelength light, affected sites in deep regions from the skin such as corium and subcutaneous tissue can receive the light, and therefore, the compositions of the present invention are useful photosensitizing agents for PDT.

The bacteriochlorin skeleton accumulated in tumor cells emit distinctive red fluorescence when irradiated with light in the Q band (about 730 nm). Therefore, the tetraphenylbacteriochlorin derivatives (I) and their salts are expected to be applied to photodynamic diagnosis (PDD) for diagnosing the presence or localization of cancer focuses.

Accordingly, the present invention provides compositions as photosensitizers containing the tetraphenylbacteriochlorin derivatives (I) or their salts.

The compositions containing the tetraphenylbacteriochlorin derivatives (I) or their salts of the present invention can be used for diagnosis and treatment of cancers and tumors. Examples of cancers and tumors include stomach cancer, intestinal cancer, lung cancer, breast cancer, uterine cancer, esophagus cancer, ovarian cancer, pancreatic cancer, pharyngeal cancer, sarcoma, liver cancer, bladder cancer, maxillary cancer, bile duct cancer, tongue cancer, brain tumor, skin cancer, malignant struma, prostate cancer, parotid cancer, Hodgkin's disease, multiple myeloma, kidney cancer, leukemia and malignant lymphocytoma.

The tetraphenylbacteriochlorin derivatives (I) and their salts may be administered to human beings and animals in the form of compositions with pharmaceutically acceptable ordinary additives. The compositions of the present invention may further contain other pharmaceuticals optionally.

The compositions of the present invention are administered orally or parentally, e.g., by intravenous injection or by intramuscular injection. They are orally administered in the form of tablets, pills, powder, granules, subtilized granules, capsules, liquid, suspension, emulsion and the like, and parentally administered in the form of injections, drops, suppositories, ointments, plasters, patches, aerosols and the like.

As pharmaceutically acceptable additives, may be used those ordinarily used in the pharmaceutical field depending upon dosage form.

For example, tablets can be produced by adding excipients (lactose, starch, crystalline cellulose, etc.), binders (liquid starch, carboxymethyl cellulose, etc.) and the like according to the conventional method.

For example, injections or drops can be prepared by dissolving the composition in distilled water for injection as a diluent, adding a pH regulator, a buffer (sodium citrate, sodium acetate, sodium phosphate, etc.), if necessary, and preparing injections or drops for intravenous, intramuscular, subcutaneous, intracutaneous and intraperitoneal injections or drops by the conventional method. Preferably, the injections and drops are sterilized and are isotonic with blood.

The dosage of the tetraphenylbacteriochlorin derivatives (I) or their salts is 7 to 0.07 mg/kg (photofrin), preferably 0.7 mg/kg (photofrin) for diagnosis of tumors, and 30 to 0.3 mg/kg HpD (photofrin), preferably 3 mg/kg HpD (photofrin) or 20 to 0.2 mg/kg PHE (photofrin), preferably 2 mg/kg PHE (photofrin) for treatment of tumors.

When the compositions of the present invention are administered, the tetraphenylbacteriochlorin derivatives (I) of the present invention or their salts are distributed selectively in tumor cells after a certain time period.

Thereafter, for diagnosing tumor, a light beam with a wavelength of 360 to 760 nm is applied to a site to be tested. A light source is not particularly limited, but a halogen lamp is preferable for a diagnosis purpose because the halogen lamp can emit light with a wide range of wavelengths at a time. The tetraphenylbacteriochlorin derivatives (I) or their salts distributed in tumor cells emit fluorescence upon receiving the light beam with a wavelength within the above-mentioned wavelength, thereby allowing diagnosis of the localization and presence of the tumor cells.

For treating tumor, the compositions containing the tetraphenylbacteriochlorin derivatives (I) or their salts are administered, and then, a light beam with a wavelength near 740 nm, or of 720 to 760 nm is applied to a site to be treated.

A light source is not particularly limited, but it is desirable to select and use one selectively emitting a strong light beam within a desired wavelength range. As light sources, a semiconductor laser or light-emitting diode such as a near-infrared laser using gallium-aluminum-arsenic, gallium-indium-arsenic-phosphorus, gallium-phosphorus or gallium-arsenic-phosphorus, a gas laser such as a krypton ion laser, a solid variable wavelength laser using alexandrite or titanium-sapphire and a dye laser using styryl, oxazin and xanthene may be mentioned.

Since the tetraphenylbacteriochlorin derivatives (I) and their salts of the present invention have a large molar extinction coefficient, the intensity of the light beam for irradiation may be weaker than in the case where conventional photosensitisers are used. Therefore, a photodynamic therapy using the tetraphenylbacteriochlorin derivatives (I) or their salts of the present invention puts a smaller load on living bodies receiving the therapy. More particularly, the irradiation intensity of the light beam may be 10 to 500 mW/cm$^2$, preferably 160 to 500 mW/cm$^2$. The number of times of irradiation with the light beam may be one or more times per day, for example, 1 to 100 times/day, preferably 1 to 10 times/day. The combination of times of the administration of the composition of the present invention with the times of irradiation with the light beam may be such that tumor is reduced significantly.

The process of producing tetraphenylbacteriochlorin derivatives (I) of the present invention is now described by way of examples, but the present invention is not limited to the examples.

The following compounds used as starting materials in the examples were prepared according to the production examples of Japanese Unexamined Patent Publication No. 2000-7693:

5,10,15,20-Tetrakis[4-(2',3',4',6'-tetra-O-acetyl-β-D-glucopyranosyloxy)phenyl]porphyrin (Production Example 3 of Japanese Unexamined Patent Publication No. 2000-7693); and 5,10,15,20-Tetrakis[4-(2',3',4',6'-tetra-O-acetyl-β-D-galactopyranosyloxy)phenyl]porphyrin (Production Example 5 of Japanese Unexamined Patent Publication No.2000-7693).

Experiments for study about preparation of tetraphenylporphyrin derivatives (V) as starting materials for synthesizing tetraphenylbacteriochlorin derivatives (I) of the present invention:

Synthesis of
5,10,15,20-tetrakis(3-methoxyphenyl)porphyrin

3-Methoxybenzaldehyde (1.6 mL, 12 mmol) was dissolved in dry chloroform (1 L) in an argon-replaced 500 mL round bottom flask equipped with a conderser. A reaction vessel was shielded from light with aluminum foil, and pyrrole (0.74 mL, 0.74 g, 11 mmol) was added to the reaction mixture through a syringe. Argon gas was introduced into the reactor with stirring. After about 30 minutes, the introduction of the gas was stopped and BF$_3$.Et$_2$O (0.3 mL, 2.4 mol) was added to the reaction mixture through a syringe. Argon replacement was carried out for 10 minutes, and the reaction mixture was stirred for an hour. Zinc acetate dihydrate (5.0 g, 23 mmol) was added to the reaction mixture and argon replacement was carried out for 10 minutes. Thereafter, the reaction mixture was stirred at room temperature for 20 to 24 hours. Subsequently, p-chloranil (2.1 g, 8.3 mmol) was added to the reaction mixture at a time and the resulting reaction mixture was stirred at 60 to 65° C. for an hour. The resulting mixture was cooled to room temperature and then concentrated under reduced pressure to about 100 mL. The obtained concentrated solution was washed with 4N—HCl (100 mL×3) (disappearance of Zn-containing substances was checked by UV), water (100 mL×3) and then with a saturated aqueous sodium hydrogen carbonate (100 mL×2). Thereafter, the resultant was dried over anhydrous sodium sulfate for 10 minutes. The resulting liquid was concentrated and purified by column chromatography (eluent:chloroform) to give the product. The obtained crude product was dissolved in chloroform, a small amount of ethanol was added until just before solid appeared, and the resulting mixture was allowed to stand in a refrigerator. The separated solid was filtered out and washed with ethanol, to give 5,10,15,20-tetrakis(3-methoxyphenyl)porphyrin as a purplish red solid. The obtained compound was characterized by $^1$H-NMR and mass spectrum. It was confirmed that the obtained compound was identical with the title compound described by D. A. James, D. P. Arnold, P. G. Parsons, *Photochem. Photobiol.*, 1994, 59, 441. Yield 1.8 g, 89%.

PRODUCTION EXAMPLE 1

2,3,4,6-tetra-O-acetyl-α-D-glucopyranosyl bromide

D-glucose (39 g, 236 mmol) was dried by a vacuum pump in a 500 mL round bottom flask overnight. Thereafter, 98 mL (71.0 g, 577 mmol) of acetyl bromide were added at a time at room temperature. Immediately after that, a condenser equipped with a calcium chloride tube was mounted and the resulting mixture was stirred vigorously at room temperature for a while. Once reaction had started, gas began to be released from the calcium chloride tube. The mixture was continuously stirred in an ice bath overnight. To the resulting yellow reaction mixture, diethyl ether (390 mL) was added via the condenser, and the resulting reaction mixture was poured in a mixture of ice (310 g) and water (120 mL). The resulting mixture was stirred vigorously. An ether phase was separated and combined with an ether phase extracted from a water phase. The combined ether phase was added to a saturated aqueous cold sodium hydrogen carbonate (390 mL), followed by vigorous stirring, and was well shaken and separated using a separatory funnel. Further the ether phase was poured into a mixture of ice (310 g) and water (120 mL), followed by vigorous stirring, and was well shaken and separated using a separatory funnel. The ether phase was dried over anhydrous sodium sulfate. The resulting liquid was concentrated and cooled in the refrigerator for crystallization. The obtained crystals were filtered by suction, washed with cold ether and dried to give the title compound. White acicular crystals. Yield 53 g, 55.6%.

$^1$H NMR (300.07 MHz, CDCl$_3$) δ: 6.62 (1H, d, J=3.9 Hz, H-1), 5.58 (1H, t, J=9.6 Hz, H-3), 5.16 (1H, t, J=9.8 Hz, H-4), 4.85 (1H, dd, J=9.9, 3.9 Hz, H-2), 4.34 (1H, dd, J=12.6, 3.9 Hz, H-6), 4.31 (1H, m, H-5), 4.14 (1H, dd, J=12.3, 2.1 Hz, H-6), 2.11 (3H, s, acetyl), 2.10 (3H, s, acetyl), 2.06 (3H, s, acetyl), 2.04 (3H, s, acetyl).

PRODUCTION EXAMPLE 2

3-(2',3',4',6'-tetra-O-acetyl-β-D-glucopyranosyloxy)-benzaldehyde

Quinoline (15 mL) was added to 1.5 g (12 mmol) of m-hydroxybenzaldehyde, to which 2,3,4,6-tetra-O-acetyl-α-D-glucopyranosyl bromide (10.1 g, 25 mmol) was added. Immediately after that, 5.8 g (25 mmol) of silver (I) oxide was added, followed by 15 minutes' stirring at room temperature. The resulting mixture generated heat with progress of reaction. Because the resulting mixture became more and more viscous during the reaction, the mixture was stirred with a glass rod as required. A 25% acetic acid (100 mL) was added to the reaction mixture, which was well stirred on ice bath, followed by filtration. Methanol (150 mL) was added to the filtered-out residue, followed by heating. Then, the resulting mixture was filtered and the obtained filtrate was concentrated until crystals separated. The resulting residue was recrystallized from hot methanol to give the title compound. Light yellow acicular crystals. Yield 3.4 g, 63%.

$^1$H NMR (300.07 MHz, CDCl$_3$) δ: 9.99 (1H, s, aldehyde), 7.59 (1H, m, benzene-6), 7.50–7.42 (2H, m, benzene-1,5), 7.26 (1H, m, benzene-4), 5.30 (2H, m, glucose-H), 5.20–5.12 (2H, m, glucose-H), 4.30–4.18 (2H, m, H-6'×2), 3.92 (1H, m, H-5'), 2.08, 2.07, 2.05 (12H, s×3, acetyl).

PRODUCTION EXAMPLE 3

5,10,15,20-tetrakis[3-(2',3',4',6'-tetra-O-acetyl-β-D-glucopyranosyl-oxy)phenyl]porphyrin 3-(2',3',4',6'-tetra-O-acetyl-β-D-glucopyranosyloxy)benzaldehyde (1.9 g, 3.8 mmol) was dissolved in 680 mL of dry chloroform in an argon-replaced 500 mL round bottom flask equipped with a conderser tube. A reaction vessel was shielded from light with aluminum foil, 0.27 mL (0.27 g, 3.8 mmol) of pyrrole were added through a syringe, and argon gas was introduced with stirring. After about 30 minutes, the introduction of the gas was stopped and BF$_3$.Et$_2$0 (0.10 mL, 0.80 mmol) was added to the reaction mixture using a syringe, followed by 10 minutes' argon replacement. After an hour, zinc acetate dihydrate (3.9 g, 17.5 mmol) was added to the reaction mixture and argon replacement was carried out for 10 minutes. The resulting mixture was stirred at room temperature for 20 to 24 hours. Subsequently, p-chloranil (0.70 g, 2.7 mmol) was added to the reaction mixture at a time and stirred at 60 to 65° C. for an hour. After reaction, the color of the liquid turned red. The mixture was cooled to room temperature and then concentrated to about 100 mL. The residue was washed with a 4N hydrochloric acid (100 mL×3), water (100 mL×3), and a saturated aqueous solution of sodium hydrogen carbonate (100 mL×2), and then dried over anhydrous sodium sulfate. About 10 g of silica gel was added to the resulting liquid, which was evaporated to dryness. Separation by silica gel column chromatography was performed (the developing solvent used was chloroform and acetone in a ratio of between 15:1 and 8:1). A dark purplish red fraction containing the product was collected and concentrated to dryness. The obtained residue was dissolved in chloroform, and a small amount of ethanol was added until solid appeared. The resultant was allowed to stand in the refrigerator. The solid was filtered and washed with ethanol, to give the title compound as a purplish red solid. Yield 1.3 g, 68%. Rf=0.55 (chloroform:ethanol=14:1). Red fluorescence was emitted at UV of 365 nm.

$^1$H NMR (300.07 MHz, DMSO-d$_6$) δ: 8.97 (8H, m, pyrrole-β), 7.95–7.75 (12H, m, benzene-6,1,5), 7.47–7.21 (4H, m, benzene-4), 5.89–5.83 (4H, m, H-1'), 5.46–5.36 (4H, m, H-2'),5.21–5.03 (4H, m, H-3'), 4.42–3.94 (4H, m, H-4'), 4.22–4.12 (4H, m, H-6'), 4.12–4.02 (4H, m, H-6'), 4.02–3.92 (4H, m, H-5'), 2.05 (12H, s, acetyl), 1.95 (12H, s, acetyl), 1.94 (12H, s, acetyl), 1.93 (12H, s, acetyl), 1.25–1.18 (m, acetyl), −3.00 (2H, s, pyrrole NH).

PRODUCTION EXAMPLE 4

3-(2',3',4',6'-tetra-O-acetyl-α-D-galactopyranosyloxy)benzaldehyde m-Hydroxybenzaldehyde (1.5 g, 12 mmol), dichloromethane (14 mL), a 5% aqueous solution of sodium hydroxide (20 mL) were put in a 100 mL round bottom flask and stirred vigorously. At that time, the water phase turned yellow. Into the resulting mixture, tetra-butylammonium bromide (0.66 g, 2.0 mmol) was added and then a solution of acetobromogalactose (3.6 g, 8.6 mmol) in dichloromethane (about 6 mL) was added dropwise. The reaction vessel was shielded from light and the resulting mixture was stirred vigorously for 2 days at room temperature. A separated organic phase was washed with a 5% aqueous solution of sodium hydroxide (20 mL×3) and then with water (20 mL×3), dried over anhydrous sodium sulfate and evaporated to dryness to give the title compound. Light brown solid. Yield 2.2 g, 39%. The product was unstable at room temperature, and stored in a freezer.

$^1$H NMR (300.07 MHz, CDCl$_3$) δ: 9.98 (1H, s, aldehyde), 7.62–7.57 (1H, m, benzene-6), 7.57–7.51 (1H, m, benzene-1), 7.51–7.47 (1H, m, benzene-5), 7.32–7.25 (1H, m, benzene-4), 5.57–5.41 (2H, m, H-2'), 5.18–5.12 (2H, m, H-1', H-2'), 4.27–4.04 (3H, m, H-5'+H-6'×2), 2.20 (3H, s, acetyl), 2.08 (3H, s, acetyl), 2.06 (3H, s, acetyl), 2.03 (3H, s, acetyl).

PRODUCTION EXAMPLE 5

5,10,15,20-tetrakis[3-(2',3',4',6'-tetra-O-acetyl-β-D-galactopyranosyloxy)phenyl]porphyrin The title compound was obtained in the same manner as in Production Example 3 except that 3-(2',3',4',6'-tetra-O-acetyl-α-D-galactopyranosyloxy)benzaldehyde was used instead of 3-(2',3',4',6'-tetra-O-acetyl-β-D-glucopyranosyloxy)benzaldehyde. Rf=0.70 (chloroform:acetone=15:1).

$^1$H NMR (300.07 MHz, CDCl$_3$) δ: 8.89 (8H, s, pyrrole-β), 7.95–7.84 (8H, m, benzene-1,6), 7.73–7.62 (4H, m, benzene-5), 7.50–7.42 (4H, m, benzene-4), 5.68–5.54 (4H, m, H-2'), 5.54–5.38 (4H, m, H-4'), 5.38–5.20 (4H, m, H-1'), 5.20–4.93 (4H, m, H-3'), 4.23–3.91 (12H, m, H-6'×2,H-5'), 2.16 (12H, s, acetyl), 2.10 (12H, s, acetyl), 2.08 (12H, s, acetyl), 2.00 (12H, s, acetyl), 1.29–1.23 (m, acetyl),–2.89 (2H, br s, pyrrole-NH).

PRODUCTION EXAMPLE 6

2,3,4-tri-O-acetyl-β-D-arabinopyranosyl bromide

Acetyl bromide 30 mL (21.7 g, 177 mmol) was added to a 100 mL round bottom flask containing D-arabinose (6.52 g, 43 mmol) at a time at room temperature. Immediately after that, a condenser tube equipped with a calcium chloride tube was attached, and the resulting mixture was stirred vigorously at room temperature. When gas started to be discharged out of the calcium chloride tube, the resulting mixture was continuously stirred in an ice bath for 2 to 3 hours. Chloroform (100 mL) was added to the yellow reaction mixture via the condenser, and then the resulting mixture was poured in a mixture of ice (50 g) and water (100 mL) and stirred vigorously. The extracted chloroform phase was combined with a chloroform phase extracted from a water phase. The combined chloroform phase was added to 100 mL of a saturated aqueous cold sodium hydrogen carbonate, followed by vigorous stirring, and was well shaken and separated using a separatory funnel. Thereafter, the organic phase was dried over calcium chloride for 10 minutes and then concentrated to 20 mL. Diethyl ether (8 mL) was added to the residue, followed by stirring. Petroleum ether (5 mL) was added gently and the resulting mixture was cooled in the freezer for crystallization. The crystals were filtered by suction, washed with cold ether and dried to give the title compound. White acicular crystals. Yield 12 g, 82%. The product was unstable at room temperature, and stored in the freezer.

$^1$H NMR (300.07 MHz, CDCl$_3$) δ: 6.71 (1H, d, J=3.6 Hz, H-1), 5.41 (2H, m, H-3, H-4), 5.09 (1H, m, J=1.5, 3.6, 12 Hz, H-2), 4.22 (1H, d, J=13.5 Hz, H-5), 3.94 (1H, dd, J=1.7, 13.2 Hz, H-5'), 2.16 (3H, s, acetyl), 2.13 (3H, s, acetyl), 2.06 (3H, s, acetyl), 2.04 (3H, s, acetyl).

PRODUCTION EXAMPLE 7

4-(2',3',4'-tri-O-acetyl-β-D-arabinopyranosyloxy)benzaldehyde p-Hydroxybenzaldehyde (2.2 g, 18 mmol), dichloromethane 18 mL, a 5% aqueous solution of sodium hydroxide (20 mL) were put in a 100 mL round bottom flask and stirred vigorously. At that time, the water phase turned yellow. To the resulting mixture, tetrabutylammonium bromide (1.0 g, 3.0 mmol) was added, and then a solution of 2,3,4-tri-O-acetyl-β-D-arabinopyranosyl bromide (4.0 g, 12 mmol) in dichloromethane (about 6 mL) was added dropwise. A reaction vessel was protected from light, and the resulting mixture was stirred vigorously at room temperature for 2 days. The separated organic phase was washed with 50 mL of a 5% aqueous solution of sodium hydroxide three times and then with 50 mL of water three times, dried over anhydrous sodium sulfate and evaporated to dryness to give the title compound. Light brown solid. Yield 1.9 g, 43%. The product was unstable at room temperature, and stored in the freezer.

$^1$H NMR (300.07 MHz, CDCl$_3$) δ: 9.92 (1H, s, aldehyde), 7.86 (2H, d, J=8.4 Hz, o-aldehyde), 7.13 (2H, d, J=8.7, m-aldehyde), 5.45 (1H, d, J=6.0, 8.1 Hz, H-2'), 5.36 (1H, m, H-4'), 5.24 (1H, d, J=6.0 Hz, H-1'), 5.20 (1H, dd, J=3.6, 8.4 Hz, H-3'), 4.13 (1H, dd, J=4.2, 12.3 Hz, H-5'), 3.81 (1H, dd, J=2.1, 12.3 Hz, H-5'), 2.14 (3H, s, acetyl), 2.13 (3H, s, acetyl), 2.11 (3H, s, acetyl).

PRODUCTION EXAMPLE 8

3-(2',3',4'-tri-O-acetyl-β-D-arabinopyranosyloxy)benzaldehyde

The title compound was obtained in the same manner as Production Example 7 except that m-hydroxybenzaldehyde was used instead of p-hydroxybenzaldehyde. Light brown solid. The product was unstable at room temperature, and stored in the freezer.

$^1$H NMR (300.07 MHz, CDCl$_3$) δ: 9.99 (1H, s, aldehyde), 7.59 (1H, d, benzene-6), 7.53 (1H, m, benzene-1), 7.51 (1H, m, benzene-5), 7.29 (1H, m, benzene-4), 5.43 (1H, dd, J=6.3, 8.7 Hz, H-2'), 5.33 (1H, m, H-4'),5.17 (1H, d, J=6.3 Hz, 2.1, 12.3 Hz, H-1'), 5.16 (1H, dd, J=4.2, 8.7 Hz, H-3'), 4.09 (1H, dd, J=4.2, 12.3 Hz, H-5'), 3.78 (1H, dd, J=2.1, 12.3 Hz, H-5'), 2.16 (3H, s, acetyl), 2.10 (3H, s, acetyl), 2.06 (3H, s, acetyl), 2.03 (3H, s, acetyl).

PRODUCTION EXAMPLE 9

5,10,15,20-tetrakis[4-(2',3',4'-tri-O-acetyl-β-D-arabinopyranosyloxy)phenyl]porphyrin The title compound was obtained in the same manner as in Production Example 3 except that 4-(2',3',4'-tri-O-acetyl-β-D-arabinopyranosyloxy)benzaldehyde was used instead of 3-(2',3',4',6'-tetra-O-acetyl-β-D-glucopyranosyloxy)benzaldehyde. Dark red solid.

$^1$H NMR (300.07 MHz, CDCl$_3$): δ: 8.85 (8H, s, pyrrole-β), 8.14 (8H,d,J=8.4 Hz, o-benzene), 7.41 (8H, d, J=8.7 Hz, m-benzene), 5.58 (4H, dd, J=6.3, 8.7 Hz, H-3'), 5.44 (8H, m, H-1', H-4'), 5.15 (4H, dd, J=9.0 Hz, H-2'), 4.32 (4H, dd, J=3.6, 11.4 Hz, H-5'), 3.96 (4H, dd, J=11.4 Hz, H-5'), 2.28 (12H, s, acetyl), 2.24 (12H, s, acetyl), 2.17 (12H, s, acetyl), −2.82 (2H, br s, pyrrole-NH).

PRODUCTION EXAMPLE 10

5,10,15,20-tetrakis[3-(2',3',4'-tri-O-acetyl-β-D-arabinopyranosyl-oxy)phenyl]porphyrin The title compound was obtained in the same manner as in Production Example 3 except that 3-(2',3',4'-tri-O-acetyl-β-D-arabinopyranosyloxy)benzaldehyde was used instead of 3-(2',3',4',6'-tetra-O-acetyl-β-D-glucopyranosyloxy)benzaldehyde. Dark red solid.

$^1$H NMR (300.07 MHz, CDCl$_3$) δ: 8.97 (8H, s, pyrrole-β), 7.89 (4H, m, benzene-1, -6), 7.68 (4H, m, benzene-5), 7.45 (4H, m, benzene-4), 5.55 (4H, t, J=8.7 Hz, H-3'), 5.37 (8H, m, H-1', H-4'), 5.18 (4H, dd, J=8.7 Hz), 4.09 (4H, m, H-5'), 3.73 (4H, d, J=12.3 Hz, H-5'), 2.12 (12H, s,acetyl), 2.10 (12H, s, acetyl), 2.04 (12H, s, acetyl), −2.87 (2H, br s, pyrrole-NH).

PRODUCTION EXAMPLE 11

1,2,3,4-tetra-O-acetyl β-D-xylose

A 200 mL round bottom flask containing sodium acetate (3.0 g) and acetic anhydride (36 mL) was heated to 130° C. on oil bath. When bubbles started to come out, D-xylose (5.0 g, 33.3 mmol) was added gradually. When bubbles did not come out any more, the flask was put away from the oil bath and cooled to room temperature. The reaction mixture was put in a 500 mL beaker containing ice (150 g), stirred for a while and then allowed to stand for 2 hours. The resultant light-brown precipitate was filtered by suction, washed with cold water and then dried by vacuum. The crude product was recrystallized using hot ethanol. The crystals were filtered by suction, washed with cold ethanol, and dried to give the title compound. White crystals. Yield 5.55 g, 53%.

$^1$H NMR (300.07 MHz, CDCl$_3$) δ: 5.72 (1H, d, J=6.9 Hz, H-1), 5.16 (1H, t, J=8.1, 8.4 Hz, H-3), 5.24 (1H, dd, J=5.1, 8.1 Hz, H-2), 4.98 (1H, m, J=5.1, 8.1, 8.4 Hz, H-4), 4.16 (1H, dd, J=5.1, 12.0 Hz, H-5), 3.53 (1H, dd, J=8.3, 12.0 Hz, H-5'), 2.12 (3H, s, acetyl), 2.07 (3H, s, acetyl), 2.06 (6H, s, acetyl).

PRODUCTION EXAMPLE 12

2,3,4-tri-O-acetyl-α-D-xylopyranosyl bromide

Acetic acid (6 mL) and a 30% hydrobromic acid-acetic acid solution (25 mL) were put in a 100 mL round bottom flask containing 1,2,3,4-tetra-O-acetyl β-D-xylose (5.0 g, 15.7 mmol) and stirred at room temperature for an hour. Chloroform (100 mL) was poured into the reaction mixture. The resulting mixture was washed with water (100 mL×2) and with a saturated aqueous solution of sodium hydrogen carbonate (100 mL×1), and dried over calcium chloride. The resulting mixture was concentrated to 20 mL. To the resulting mixture, diethyl ether (8 mL) was added, followed by stirring. Petroleum ether (5 mL) was quietly added to the resulting mixture, which was cooled in the freezer for crystallization. The crystals are filtered by suction, washed with cold ether and dried to give the title compound. White acicular crystals. Yield 4.6 g, 87%. The product was unstable at room temperature, and stored in the freezer.

$^1$H NMR (300.07 MHz, CDCl$_3$) δ: 6.56 (1H, d, J=3.9 Hz, H-1), 5.57 (1H, t, J=9.6, 9.8 Hz, H-3), 5.04 (1H, m, J=11.1 Hz, H-4), 4.78 (1H, dd, J=3.9, 9.8 Hz, H-2), 4.06 (1H, dd, J=6.3, 11.1 Hz, H-5), 3.88 (1H, t, J=11.1, 11.1 Hz, H-5'), 2.13 (3H, s, acetyl), 2.69 (3H, s, acetyl), 2.09 (3H, s, acetyl).

PRODUCTION EXAMPLE 13

4-(2',3',4'-tri-O-acetyl-β-D-xylopyranosyloxy)benzaldehyde p-Hydroxybenzaldehyde (2.2 g, 18 mmol), dichloromethane (20 mL) and a 5% aqueous solution of sodium hydroxide (25 mL) were put in a 100 mL round bottom flask and stirred vigorously. At that time, the water phase turned yellow. To the resulting mixture, tetrabutylammonium bromide (1.0 g, 3.0 mmol) was added, and then, a dichloromethane (about 6 mL) solution of 2,3,4-tri-O-acetyl-α-D-xylopyranosyl bromide (4.0 g, 12 mmol) was added dropwise. The reaction vessel was protected from light. The resulting mixture was stirred vigorously at room temperature for 2 days. The separated organic phase was washed with 50 mL of a 5% aqueous solution of sodium hydroxide three times and then with 50 mL of water three times, dried over anhydrous sodium sulfate and evaporated to dryness to give the title compound. Light brown solid. Yield 1.5 g, 34%. The product was unstable at room temperature, and stored in the freezer.

$^1$H NMR (300.07 MHz, CDCl$_3$) δ: 9.93 (1H, s, aldehyde), 7.64 (2H, d, J=8.4 Hz, o-aldehyde), 7.12 (2H, d, J=8.7, m-aldehyde), 5.34 (1H, d, J=5.1 Hz, H-1'), 5.25 (1H, dd, J=7.5 Hz, H-3'), 5.20 (1H, dd, J=5.4, 7.5 Hz, H-2'), 5.01 (1H, m, H-4'), 4.24 (1H, dd, J=4.2, 12.3 Hz, H-5'), 3.61 (1H,dd, J=6.9, 12.3 Hz, H-5'), 2.14 (3H, s, acetyl), 2.13 (3H, s, acetyl), 2.10 (3H, s, acetyl).

PRODUCTION EXAMPLE 14

3-(2',3',4'-tri-O-acetyl-β-D-xylopyranosyloxy)benzaldehyde

The title compound was obtained in the same manner as in Production Example 13 except that m-hydroxybenzaldehyde was used instead of p-hydroxybenzaldehyde. Light brown solid. The product was unstable at room temperature, and stored in the freezer.

$^1$H NMR (300.07 MHz, CDCl$_3$) δ: 9.99 (1H, s, aldehyde), 7.61 (1H, d, J=8.4, benzene-6), 7.52 (1H, s, benzene-1), 7.51 (1H, t, J=7.8, 10.5 Hz, benzene-5), 7.28 (1H, d, J=10.5 Hz, benzene-5), 5.43 (1H, dd, J=6.3, 8.7 Hz, H-2'), 5.33 (1H, m, H-4'), 5.17 (1H, d, J=6.3 Hz, H-1'), 5.16 (1H, dd, J=4.2, 8.7 Hz, H-3'), 4.09 (1H, dd, J=4.2, 12.3 Hz, H-5'), 3.78 (1H, dd, J=2.1, 12.3 Hz, H-5'), 2.15 (3H, s, acetyl), 2.11 (3H, s, acetyl), 2.08 (3H, s, acetyl).

PRODUCTION EXAMPLE 15

5,10,15,20-tetrakis[4-(2',3',4'-tri-O-acetyl-β-D-xylopyranosyloxy)-phenyl]porphyrin The title compound was obtained in the same manner as in Production Example 3 except that 4-(2',3',4'-tri-O-acetyl-β-D-xylopyranosyloxy)benzaldehyde was used instead of 3-(2', 3',4',6'-tetra-O-acetyl-β-D-glucopyranosyloxy)benzaldehyde. Dark red solid.

¹H NMR (300.07 MHz, CDCl₃) δ: 8.96 (8H, s, pyrrole-β), 8.14 (8H,d,o-benzene), 7.39 (8H, d, J=8.4 Hz, m-benzene), 5.54 (4H, t, J=6.0 Hz, H-2'), 5.39–5.37 (8H, m, H-1', H-3'), 5.15 (4H, m, J=4.8 Hz, H-4'), 4.43 (4H, dd, J=4.8, 12.3 Hz, H-5'), 3.73 (4H, dd, J=7.8, 12.3 Hz, H5'), 2.22 (12H, s, acetyl), 2.17 (12H, s, acetyl), 2.13 (12H, s, acetyl), −2.91 (2H, br s, pyrrole-NH).

PRODUCTION EXAMPLE 16

5,10,15,20-tetrakis[3-(2',3',4'-tri-O-acetyl-β-D-xylopyranosyloxy)-phenyl]porphyrin The title compound was obtained in the same manner as in Production Example 3 except that 3-(2',3',4'-tri-O-acetyl-β-D-xylopyranosyloxy)benzaldehyde was used instead of 3-(2',3',4',6'-tetra-O-acetyl-8-D-glucopyranosyloxy)benzaldehyde. Dark red solid.

¹H NMR (300.07 MHz, CDCl₃) δ: 8.97 (8H, s, pyrrole-β), 7.93 (4H, m, benzene-1), 7.87 (4H, m, benzene-6), 7.68 (4H, m, benzene-5), 7.43 (4H, m, benzene-4), 5.38 (4H, m, H-2'), 5.25 (8H, m, H-1', H-3'), 5.05 (4H, m, H-4'), 4.26 (4H, m, H-5'), 3.57 (4H, m, H5'), 2.12 (12H, s, acetyl), 2.06 (12H, s, acetyl), 2.04 (12H, s, acetyl), −2.88 (2H, br s, pyrrole-NH).

EXAMPLE 1

5,10,15,20-tetrakis[4-(2',3',4',6'-tetra-O-acetyl-β-D-glucopyranosyloxy)phenyl]bacteriochlorin (Compound 1)

5,10,15,20-tetrakis[4-(2',3',4',6'-tetra-O-acetyl-β-D-glucopyranosyloxy)phenyl]porphyrin (0.80 g, 0.40 mmol), anhydrous potassium carbonate (1.54 g, 11 mmol), p-toluenesulfonylhydrazide (0.51 g, 2.7 mmol) and pyridine (74 mL) were put in a 100 mL three-neck flask equipped with a Dimroth condenser and protected from light with aluminum foil. The atmosphere inside was sufficiently replaced with nitrogen gas for about 20 minutes with stirring. The resulting mixture was heated under reflux at 110° C. in a nitrogen atmosphere for 9 hours. While heating under reflux, 2 mL of a solution of p-toluenesulfonylhydrazide (2.5 g, 13 mmol) in pyridine (10 mL) were added to the reaction mixture every 1.5 hours. The reaction mixture was cooled to room temperature, and then benzene (200 mL) and water (100 mL) were added to the reaction mixture. An organic phase was separated and washed successively with a 2N cold hydrochloric acid (400 mL×2), with water (400 mL×1), and with a saturated aqueous solution of sodium hydrogen carbonate (400 mL×1). The organic phase was dried over anhydrous sodium sulfate and evaporated to dryness under a reduced pressure. The obtained residue was dissolved in chloroform, and ethanol was added for separation at a low temperature. The precipitate was filtered and washed with ethanol, followed by drying, to give the title compound as a red solid (0.31 g, 39%).

¹H NMR (600 MHz, DMSO-d₆) δ: 7.8718 (4H, s, β-pyrrole), 7.7732–7.7460 (8H, m, benzene-O), 7.3355–7.2534 (8H, m, benzenem), 5.7878–5.7759 (4H, m, Glc-H1), 5.5107–5.5837 (4H, m, Glc-H3), 5.1884–5.1511 (4H, m, Glc-H2), 5.1185–4.9472 (4H, m, Glc-H4), 4.1534–4.1256 (4H, m, Glc-H5), 4.0432–4.0130 (4H, m, Glc-H6), 3.9013 (8H, s, H2, H3, H12, H13), 2.1091 (6H, s, acetyl×2), 2.0423 (6H, s, acetyl×2), 2.0334 (6H, s, acetyl×2), 2.0047 (6H, s, acetyl×2), −1.4622 (2H, br s, W1/2=5 Hz, pyrrole-NH).

EXAMPLE 2

5,10,15,20-tetrakis[3-(2',3',4',6'-tetra-O-acetyl-β-D-glucopyranosyloxy)phenyl]bacteriochlorin (Compound 2)

The title compound was obtained in the same manner as in Example 1 except that 5,10,15,20-tetrakis[3-(2',3',4',6'-tetra-O-acetyl-β-D-glucopyranosyloxy)phenyl]porphyrin was used instead of 5,10,15,20-tetrakis[4-(2',3',4',6'-tetra-O-acetyl-β-D-glucopyranosyloxy)phenyl]porphyrin.

¹H NMR (600 MHz, DMSO-d₆) δ: 7.9478–7.9087 (4H, s, β-pyrrole), 7.6969–7.6386 (4H, m, Ar-5'), 7.5202–7.4219 (8H, m, Ar-6', 1'), 7.2855–7.2498 (4H, m, Ar-4'), 5.5281–5.4774 (4H, m, Glc-H1), 5.288–5.0864 (4H, m, Glc-H2, H3), 4.9714–4.9210 (4H, m, Glc-H4), 4.1626 (8H, m, H2, H3, H112, H13), 4.0927–3.8983 (4H, m, Glc-H6'), 2.0276 (6H, s, acetyl×2), 1.9830 (6H, s, acetyl×2), 1.9431 (12H, s, acetyl×4), −1.520 (2H, br s, W1/2=5 Hz, pyrrole-NH).

EXAMPLE 3

5,10,15,20-tetrakis[4-(2',3',4',6'-tetra-O-acetyl-β-D-galactopyranosyloxy)phenyl]bacteriochlorin (Compound 3)

The title compound was obtained in the same manner as in Example 1 except that 5,10,15,20-tetrakis[4-(2',3',4',6'-tetra-O-acetyl-β-D-galactopyranosyloxy)phenyl]porphyrin was used instead of 5,10,15,20-tetrakis[4-(2',3',4',6'-tetra-O-acetyl-β-D-glucopyranosyloxy)phenyl]porphyrin.

¹H NMR (600 MHz, DMSO-d₆) δ: 7.8809 (4H, s, β-pyrrole), 7.7762–7.7549 (8H, m, benzene-O), 7.3395–7.2848 (8H, m, benzenem), 5.8372–5.8024 (4H, m, Gal-H1), 5.5058–5.4731 (4H, m, Gal-H3), 5.1957–5.1661 (4H, m, Gal-H3), 5.1957–5.1661 (4H, m, Gal-H3), 5.0870–5.0545 (4H, m, Gal-H4), 4.3640–4.3475 (4H, m, Gal-H5), 4.2846–4.2553 (4H, m, Gal-H6), 4.1519–4.1351 (4H, m, Gal-H5), 3.9089 (8H, s, H2, H3, H12, H13), 2.1424–2.0648 (6H, m, acetyl×2), 2.0423–2.0133 (12H, m, acetyl×4), 2.0133–1.9892 (6H, m, acetyl×2), −1.4561 (2H, br s, W1/2=5 Hz, pyrrole-NH).

EXAMPLE 4

5,10,15,20-tetrakis[3-(2',3',4',6'-tetra-O-acetyl-β-D-galactopyranosyloxy)phenyl]bacteriochlorin (Compound 4)

The title compound was obtained in the same manner as in Example 1 except that 5,10,15,20-tetrakis[3-(2',3',4',6'-tetra-O-acetyl-β-D-galactopyranosyloxy)phenyl]porphyrin was used instead of 5,10,15,20-tetrakis[4-(2',3',4',6'-tetra-O-acetyl-β-D-glucopyranosyloxy)phenyl]porphyrin.

¹H NMR (300 MHz, DMSO-d₆) δ: 7.38 (4H, m, β-pyrrole), 7.21 (4H, m, Ar-5'), 7.03 (8H, m, Ar-6'), 6.85 (4H, m, Ar-4'), 6.10–5.78 (4H, m, Gal-H1), 5.78–5.64 (4H, m, Gal-H3), 5.64–5.49 (4H, m, Gal-H2), 5.49–5.26 (4H, m, Gal-H4), 4.379 (12H, m, Gal-H1, H6, H5), 4.06 (4H, m, H2, H3, H12, H13, Gal-H5), 2.50 (6H, m, acetyl×2), 2.13 (12H, m, acetyl×4), 2.04 (3H, m, acetyl×2), 1.94 (3H, m, acetylx 2), −1.511 (2H, br s, W1/2=5 Hz, pyrrole-NH).

EXAMPLE 5

5,10,15,20-tetrakis[4-(2',3',4'-tri-O-acetyl-β-D-arabino-pyranosyloxy)phenyl]bacteriochlorin (Compound 5)

The title compound was obtained in the same manner as in Example 1 except that 5,10,15,20-tetrakis[4-(2',3',4'-tri-O-acetyl-β-D-arabinopyranosyloxy)phenyl]porphyrin was used instead of 5,10,15,20-tetrakis[4-(2',3',4',6'-tetra-O-acetyl-β-D-glucopyranosyloxy)phenyl]porphyrin.

$^1$H NMR (300 MHz, DMSO-$d_6$) δ: 7.87 (4H, m, β-pyrrole), 7.42–7.31 (8H, m, benzene-O), 7.12–7.31 (8H, m, benzene-m), 5.49–5.40 (4H, m, Ara-H3), 5.12–5.01 (6H, m, Ara-H1, H4), 4.09–4.73 (6H, m, Ara-H5, H2), 3.723–3.68 (8H, m, H2, H3, H12, H13), 2.41–1.60 (18H, s, acetyl×2), −1.54 (2H, br s, W1/2=5 Hz, pyrrole-NH).

EXAMPLE 6

5,10,15,20-tetrakis[3-(2',3',4'-tri-O-acetyl-β-D-arabino-pyranosyloxy)phenyl]bacteriochlorin (Compound 6)

The title compound was obtained in the same manner as in Example 1 except that 5,10,15,20-tetrakis[3-(2',3',4'-tri-O-acetyl-β-D-arabinopyranosyloxy)phenyl]porphyrin was used instead of 5,10,15,20-tetrakis[4-(2',3',4',6'-tetra-O-acetyl-β-D-glucopyranosyloxy) phenyl]porphyrin.

$^1$H NMR (600 MHz, DMSO-$d_6$) δ: 7.9645 (4H, m, β-pyrrole), 7.5802–7.57704 (4H, m, Ar-5'), 7.5579–7.263 (12H, m, Ar-4', 6',1'), 5.4956–5.4257 (4H, m, Ara-H3), 5.3036–5.2676 (3H, m, Ar—H4), 5.0576–4.9795 (3H, m, Ara-H5, H2), 4.1982–3.9778 (6H, m, Ara-H5, H2), 3.7797–3.6842 (8H, m, H2, H3, H12, H13), 2.1572–2.1145 (6H, m, acetyl×2), 2.20672–2.1145 (6H, m, acetyl×2), 2.0544–2.0443 (6H, m, acetyl×2), −1.4797 (2H, br s, W1/2=5 Hz, pyrrole-NH).

EXAMPLE 7

5,10,15,20-tetrakis[4-(2',3',4'-tri-O-acetyl-β-D-xylopyranosyloxy)phenyl]bacteriochlorin (Compound 7)

The title compound was obtained in the same manner as in Example 1 except that 5,10,15,20-tetrakis[4-(2',3',4'-tri-O-acetyl-β-D-xylopyranosyloxy)phenyl]porphyrin was used instead of 5,10,15,20-tetrakis[4-(2',3',4',6'-tetra-O-acetyl-β-D-glucopyranosyloxy)phenyl]porphyrin.

$^1$H NMR (300 MHz, DMSO-$d_6$) δ: 7.79 (4H, m, β-pyrrole), 7.82 (8H, m, benzene-O), 7.59–7.33 (8H, m, benzene-m), 7.33–7.18 (4H, m, Ar-4'), 5.76–5.61 (4H, m, Ara-H2), 5.48–4.92 (8H, m, Ara-H3, H1), 4.15–3.78 (4H, m, H5), 3.80 (8H, m, H2, H3, H12, H13), 2.53–2.41 (18H, s, acetyl×6), −1.48 (2H, br s, W1/2=5 Hz, pyrrole-NH).

EXAMPLE 8

5,10,15,20-tetrakis[3-(2',3',4'-tri-O-acetyl-β-D-xylopyranosyloxy)-phenyl]bacteriochlorin (Compound 8)

The title compound was obtained in the same manner as in Example 1 except that 5,10,15,20-tetrakis[3-(2',3',4'-tri-O-acetyl-β-D-xylopyranosyloxy)phenyl]porphyrin was used instead of 5,10,15,20-tetrakis[4-(2',3',4',6'-tetra-O-acetyl-β-D-glucopyranosyloxy)phenyl]porphyrin.

$^1$H NMR (300 MHz, DMSO-$d_6$) δ: 7.92 (4H, m, β-pyrrole), 7.90–7.59 (8H, m, Ar-5'), 7.59–7.33 (8H, m, Ar-6', 1'), 7.33–7.18 (4H, m, Ar-4'), 5.81–5.61 (4H, m, Ara-H2), 5.43–5.19 (4H, m, Ara-H3), 5.19–5.00 (4H, m, Ara-H1), 4.15–3.78 (4H, m, H5), 3.54–3.19 (8H, m, H2, H3, H12, H13), 2.50–2.42 (18H, s, acetyl×6), −1.53 (2H, br s, W1/2=5 Hz, pyrrole-NH).

EXAMPLE 9

5,10,15,20-tetrakis[4-(β-D-glucopyranosyloxy)phenyl]-bacteriochlorin (Compound 9)

A chloroform (9 mL) solution of 5,10,15,20-tetrakis[4-(2',3',4',6'-tetra-O-acetyl-β-D-glucopyranosyloxy)phenyl] bacteriochlorin (95 mg, 0.05 mmol) was put in a 20 mL flask, and methanol (3 mL) was added thereto. Sodium methoxide was added to the resulting solution until the liquid became alkali. The resulting mixture was heated under reflux for an hour, cooled to room temperature, and then neutralized with a 25% acetic acid. The resulting mixture was cooled in ice bath for an hour, and then evaporated to dryness under a reduced pressure. The obtained residue was washed with a mixture of cold chloroform and methanol (chloroform:methanol=4:3) and dried to give the title compound (9.8 mg, 15%).

$^1$H NMR (300 MHz, DMSO-$d_6$) δ: 7.86 (4H, s, β-pyrrole), 7.77–7.75 (8H, m, benzene-O), 7.21 (8H, m, benzene-m), 5.62–5.36 (4H, m, Glc-OH), 5.36–5.26 (4H, m, H1', H2', H3', H4', H5'), 5.27–5.10 (4H, m, Glc-OH), 5.10–5.01 (4H, m, Glc-OH), 4.86–4.58 (4H, m, 6'-OH), 4.19–4.02 (4H, m, H6'), 3.68–3.34 (12H, m, H6', H1', H2', H3', H4', H5'), 3.68–3.34 (8H, s, H2, H3, H12, H13), −1.46 (2H, br s, pyrrole-NH).

EXAMPLE 10

5,10,15,20-tetrakis[3-(β-D-glucopyranosyloxy)phenyl]-bacteriochlorin (Compound 10)

The title compound was obtained in the same manner as in Example 9 except that 5,10,15,20-tetrakis[3-(2',3',4',6'-tetra-O-acetyl-β-D-glucopyranosyloxy)phenyl]bacteriochlorin was used instead of 5,10,15,20-tetrakis[4-(2',3',4',6'-tetra-O-acetyl-β-D-glucopyranosyloxy) phenyl] bacteriochlorin.

$^1$H NMR (300 MHz, DMSO-$d_6$) δ: 8.00 (4H, s, β-pyrrole) 7.61–7.59 (12H, m, Ar-6', 1',5'), 7.27–7.25 (4H, m, Ar-4'), 5.18–5.17 (4H, m, Glc-OH), 5.17–4.98 (4H, m, H1', H2', H3', H4', H5'), 4.27–3.88 (4H, m, Glc-OH), 4.13 (8H, s, H2, H3, H12, H13), 3.875–3.571 (4H, m, Glc-OH), 3.57–3.36 (8H, m, Glc-OH, 6'-OH), 3.36–3.24 (12H, m, H6', H1', H2', H3', H4', H5'), −1.46 (2H pyrrole-NH).

EXAMPLE 11

5,10,15,20-tetrakis[4-(β-D-galacto-pyranosyloxy)phenyl]-bacteriochlorin (Compound 11)

The title compound was obtained in the same manner as in Example 9 except that 5,10,15,20-tetrakis[4-(2',3',4',6'-tetra-O-acetyl-β-D-galactopyranosyloxy)phenyl]bacteriochlorin was used instead of 5,10,15,20-tetrakis[4-(2',3',4',6'-tetra-O-acetyl-β-D-glucopyranosyloxy) phenyl] bacteriochlorin.

$^1$H NMR (300 MHz, DMSO-$d_6$) δ: 8.11 (4H, m, β-pyrrole), 7.49–7.37 (8H, m, benzene-O), 7.03–6.89 (8H, m, benzene-m), 5.55–5.29 (4H, m, Gal-OH), 5.30–5.08 (4H, m, Gal-1,5), 5.08–4.82 (4H, m, Gal-OH), 4.82–4.67 (4H, m, Gal-OH), 4.67–4.50 (4H, m, Gal-OH), 4.20 (8H, s, H2, H3, H12, H13), 3.80–3.69 (4H, m, Gal-H), 3.69–3.53 (8H, m, Gal-H), 3.16 (12H, m, Gal-H), −1.45 (2H, br s, pyrrole-NH).

EXAMPLE 12

5,10,15,20-tetrakis[3-(β-D-galactopyranosyloxy) phenyl]-bacteriochlorin (Compound 12)

The title compound was obtained in the same manner as in Example 9 except that 5,10,15,20-tetrakis[3-(2',3',4',6'-tetra-O-acetyl-β-D-galactopyranosyloxy)phenyl]bacteriochlorin was used instead of 5,10,15,20-tetrakis[4-(2',3',4',6'-tetra-O-acetyl-β-D-glucopyranosyloxy)phenyl]bacteriochlorin.

$^1$H NMR (300 MHz, DMSO-$d_6$) δ: 7.82–7.79 (4H, s, β-pyrrole), 7.41–7.31 (4H, m, Ar-5'), 7.20–7.28 (8H, m, Ar-1', 6'), 7.14–7.05 (4H, m, Ar-4'), 5.67–4.86 (12H, m, Gal-OH, Gal-1,5), 4.79–4.21 (16H, m, Gal-OH, H2, H3, H12, H13), 4.15–4.06 (24H, m, Gal-H), −1.48 (2H, br s, pyrrole-NH).

EXAMPLE 13

5,10,15,20-tetrakis[4-(β-D-arabinopyranosyloxy) phenyl]-bacteriochlorin (Compound 13)

The title compound was obtained in the same manner as in Example 9 except that 5,10,15,20-tetrakis[4-(2',3',4'-tri-O-acetyl-β-D-arabinopyranosyloxy)phenyl]bacteriochlorin was used instead of 5,10,15,20-tetrakis[4-(2',3',4',6'-tetra-O-acetyl-β-D-glucopyranosyloxy)phenyl]bacteriochlorin.

$^1$H NMR (300 MHz, DMSO-$d_6$) δ: 7.79 (4H, m, β-pyrrole), 7.85 (8H, m, benzene-O), 7.38–7.34 (8H, m, benzene-m), 5.67–5.12 (6H, m, Ara-OH), 4.96–3.81 (6H, m, Ara-OH), 3.68 (8H, s, H2, H3, H12, H13), 3.76–3.13 (24H, m, Ara-H), −1.48 (2H, br s, W1/2=5 Hz, pyrrole-NH).

EXAMPLE 14

5,10,15,20-tetrakis[3-(β-D-arabinopyranosyloxy) phenyl]-bacteriochlorin (Compound 14)

The title compound was obtained in the same manner as in Example 9 except that 10,15,20-tetrakis[3-(2',3',4'-tri-O-acetyl-β-D-arabinopyranosyloxy)phenyl]bacteriochlorin was used instead of 5,10,15,20-tetrakis[4-(2',3',4',6'-tetra-O-acetyl-β-D-glucopyranosyloxy)phenyl]bacteriochlorin.

$^1$H NMR (300 MHz, DMSO-$d_6$) δ: 7.89 (4H, m, β-pyrrole), 7.55–7.45 (4H, m, Ar-5'), 7.37–7.17 (12H, m, Ar-4', 6',1'), 5.64–4.11 (12H, m, Ara-OH), 3.73–3.01 (24H, m, Ara-H, H2, H3, H12, H13), −1.51 (2H, br s, W1/2=5 Hz, pyrrole-NH).

EXAMPLE 15

5,10,15,20-tetrakis[4-(β-D-xylopyranosyloxy)phenyl]bacteriochlorin (Compound 15)

The title compound was obtained in the same manner as in Example 9 except that 5,10,15,20-tetrakis[4-(2',3',4'-tri-O-acetyl-β-D-xylopyranosyloxy)phenyl]bacteriochlorin was used instead of 5,10,15,20-tetrakis[4-(2',3',4',6'-tetra-O-acetyl-β-D-glucopyranosyloxy) phenyl]bacteriochlorin.

$^1$H NMR (300 MHz, DMSO-$d_6$) δ: 8.13 (4H, m, β-pyrrole), 7.55–7.35 (8H, m, benzene-O), 7.28–7.17 (8H, m, benzene-m), 5.62–4.48 (6H, m, Xyl-OH), 4.05–3.81 (6H, m, Xyl-OH), 3.81–2.92 (24H, m; Ara-H, H2, H3, H12, H13), −1.48 (2H, br s, W1/2=5 Hz, pyrrole-NH).

EXAMPLE 16

5,10,15,20-tetrakis[3-(β-D-xylopyranosyloxy)phenyl]bacteriochlorin (Compound 16)

The title compound was obtained in the same manner as in Example 9 except that 5,10,15,20-tetrakis[3-(2',3',4'-tri-O-acetyl-β-D-xylopyranosyloxy)phenyl]bacteriochlorin was used instead of 5,10,15,20-tetrakis[4-(2',3',4',6'-tetra-O-acetyl-β-D-glucopyranosyloxy)phenyl]bacteriochlorin.

$^1$H NMR (300 MHz, DMSO-$d_6$) δ: 7.96 (4H, m, β-pyrrole), 7.88–7.59 (8H, m, Ar-5'), 7.59–7.23 (8H, m, Ar-6', 1'), 7.23–7.18 (4H, m, Ar-4'), 5.81–4.98 (4H, m, Xyl-OH), 4.05–3.81 (6H, m, Xyl-OH), 3.81–2.80 (24H, m, Ara-H, H2, H3, H12, H13), −1.50 (2H, br s, W1/2=5 Hz, pyrrole-NH).

FIG. 1 shows data of the UV absorption of Compounds 1, 2, 9 and 10 in DMSO at 20° C. As clearly shown in FIG. 1, the compounds of the present invention have a strong UV absorption peak around 740 nm. Compounds 3 to 8 and 11 to 16 show an UV absorption pattern similar to that of tetraphenylbacteriochlorin and also have a strong UV absorption peak around 740 nm.

TEST EXAMPLE 1

Phototoxicity Test

Figure 2:
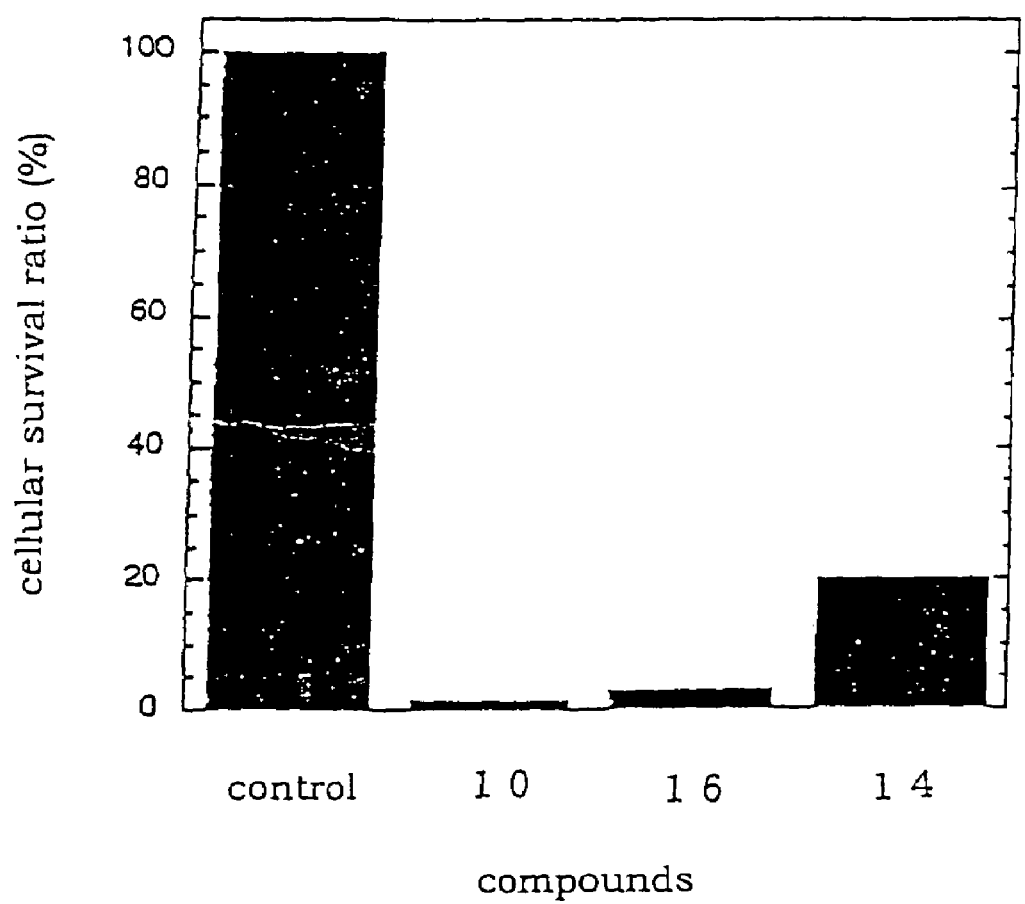
FIG. 2 is a graph showing results of testing phototoxicity of test compounds of the present invention to HeLa cells.

Each of Compounds 1 to 16 was evaluated about its cytotoxicity by viability of HeLa cells using MTT assay (Carmichal, J., W. G. DeGraff, A. F. Gazdar, J. D. Minna and J. B. Mitchell, Cancer Res., 1987, 47, 936–942). HeLa cells ($1 \times 10^4$ cells/well) were incubated in Dulbecco's modified Eagle's medium (DMEM) containing 10% fetal bovine serum (FBS) on a 96-well plate in 5% $CO_2$ at 37° C. for 24 hours. After washing with phosphate buffered saline (PBS), the cells were incubated in DMEM without serum in the presence of each of the compounds to be tested (5 or 10 μM) for two hours. The cells were washed with PBS and irradiated with a 500 W halogen lamp equipped with a filter cutting off the light shorter than 500 nm wave length for 8 minutes. After 24 hours' incubation, the viability was measured by the MTT assay. HeLa cells without test compound were used as a control. FIG. 2 shows the results of the phototoxicity test after irradiation. The survival ratio of the cells is calculated by the following formula: Cell survival ratio (%)=(OD540 in presence of test compound with irradiation/OD540 in presence of test compound without irradiation)×100. A cell survival ratio of 100% means the absence of cytotoxicity. FIG. 2 clearly shows that Compounds 10, 16 or 14 exhibited cytotoxicity when irradiated with light.

INDUSTRIAL APPLICABILITY

The tetraphenylbacteriochlorin derivatives and their salts of the present invention have a large molar extinction coefficient at long wavelengths which are expected to have a high tissue-penetrating property, and exhibit high selectivity to tumor cells and hydorphilicity.

In addition, the tetraphenylbacteriochlorin derivatives (I) and their salts of the present invention are usable as pressure sensitive coatings.

What is claimed is:

1. A tetraphenylbacteriochlorin derivative represented by the formula (I):

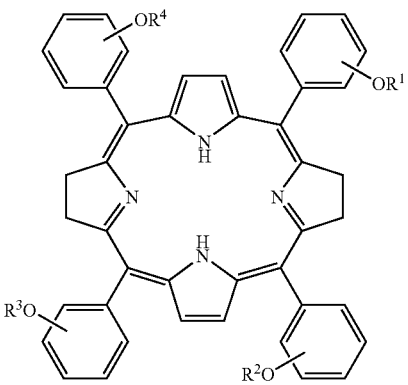
(I)

[wherein $R^1$, $R^2$, $R^3$ and $R^4$, independently from each other, are residues of mono-saccharides represented by the formulae:

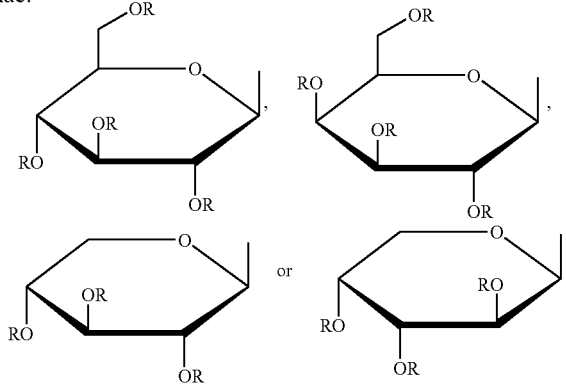

(wherein R is a hydrogen atom or a protecting group)], or its salt.

2. A salt of the tetraphenylbacteriochlorin derivative according to claim 1, which is an inner complex salt with a metal.

3. A composition for a photosensitizing agent comprising a tetraphenylbacteriochlorin derivative or its salt as set forth in claim 1 or 2.

4. A Composition according to claim 3 for use in photodynamic therapy.

5. A process for preparing a tetraphenylporphyrin derivative represented by formula (IV) and optionally formula (V), wherein the tetraphenylporphyrin derivative of formula (V) has the following structure:

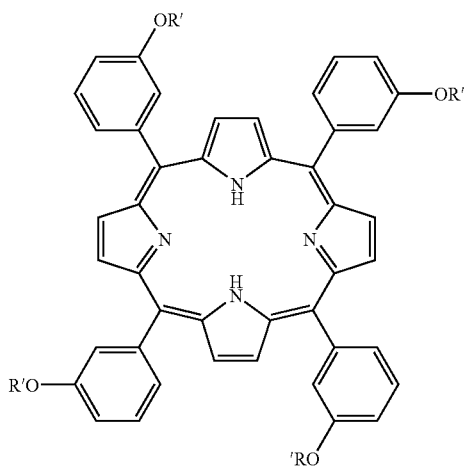
(V)

[wherein R' is a hydrogen atom, an alkyl group or a residue of a monosaccharide represented by the formula:

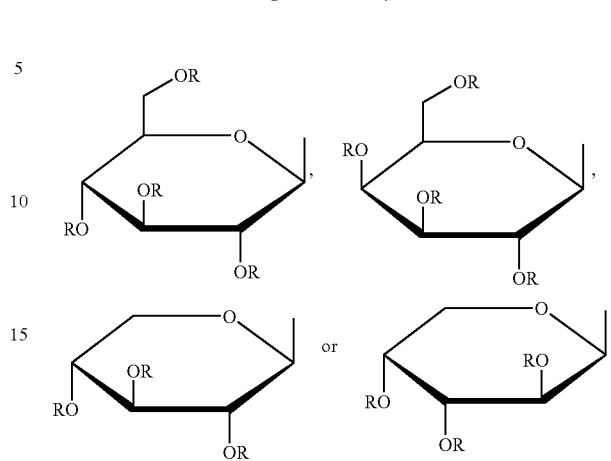

(wherein R is a hydrogen atom or a protecting group)] said process comprising reacting pyrrole with a benzaldehyde derivative represented by the formula (III):

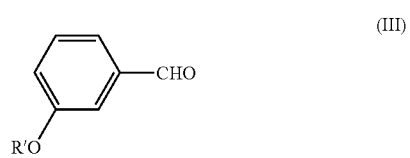
(III)

[wherein R' is as defined above] in the presence of a metal compound containing a metal selected from the group I transition metals of the periodic table of elements, to obtain a tetraphenylporphyrin derivative represented by the formula (IV):

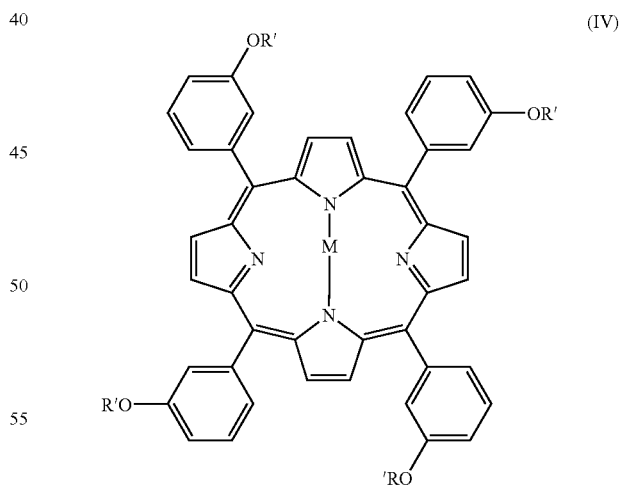
(IV)

(wherein M represents a metal selected from the group 1 transition metals of the periodic table and R' is as defined above), and optionally, demetalizing a tetraphenylporphyrin derivative of the formula (IV) to obtain the tetraphenylporphyrin derivative represented by the above formula (V).

* * * * *